United States Patent
Simonsen et al.

(10) Patent No.: US 10,829,721 B2
(45) Date of Patent: Nov. 10, 2020

(54) PARTICULATE COMPOSITION

(75) Inventors: Ole Simonsen, Soeborg (DK); Carsten Hoerslev Hansen, Vaerloese (DK); Luise Erlandsen, Frederikssund (DK)

(73) Assignee: Novozymes A/S, Bagsvaerd (DK)

(*) Notice: Subject to any disclaimer, the term of this patent is extended or adjusted under 35 U.S.C. 154(b) by 8 days.

(21) Appl. No.: 14/127,712

(22) PCT Filed: Jun. 14, 2012

(86) PCT No.: PCT/EP2012/061307
§ 371 (c)(1),
(2), (4) Date: Mar. 17, 2014

(87) PCT Pub. No.: WO2012/175401
PCT Pub. Date: Dec. 27, 2012

(65) Prior Publication Data
US 2014/0206593 A1 Jul. 24, 2014

Related U.S. Application Data

(60) Provisional application No. 61/498,763, filed on Jun. 20, 2011.

(30) Foreign Application Priority Data

Jun. 20, 2011 (EP) .................. 11170520

(51) Int. Cl.
| C11D 3/386 | (2006.01) |
| C12N 9/98 | (2006.01) |
| C11D 3/39 | (2006.01) |
| C11D 17/00 | (2006.01) |

(52) U.S. Cl.
CPC ...... *C11D 3/38627* (2013.01); *C11D 3/38672* (2013.01); *C11D 3/3932* (2013.01); *C11D 17/0039* (2013.01); *C12N 9/98* (2013.01)

(58) Field of Classification Search
CPC ......... C12S 9/00; C11D 17/06; C11D 3/3932; C11D 3/38627; C11D 17/0039; C12N 9/98
USPC ....... 510/276, 320, 351, 356, 360, 376, 392, 510/509
See application file for complete search history.

(56) References Cited

U.S. PATENT DOCUMENTS

| 4,374,035 A * | 2/1983 | Bossu ................. C11D 3/2075 206/484.1 |
| 4,391,723 A * | 7/1983 | Bacon ................. C11D 17/046 252/186.1 |
| 4,965,012 A * | 10/1990 | Olson ................ C11D 3/38672 252/186.25 |
| 5,925,609 A * | 7/1999 | Baillely ................. C11D 3/361 510/305 |
| 6,656,898 B1 * | 12/2003 | Foley et al. .................. 510/393 |
| 6,878,680 B2 * | 4/2005 | Kitko ................... C11D 3/2075 510/311 |
| 7,910,533 B2 * | 3/2011 | Somerville Roberts et al. .......... 510/276 |
| 2010/0227788 A1 | 9/2010 | Schmiedel et al. |

FOREIGN PATENT DOCUMENTS

| EP | 0723006 A2 | 7/1996 |
| GB | 2267911 A | 12/1993 |
| WO | 95/28466 A1 | 10/1995 |
| WO | 95/28468 A1 | 10/1995 |
| WO | 95/28469 A1 | 10/1995 |
| WO | 1997/16076 A1 | 5/1997 |
| WO | 97/23606 A1 | 7/1997 |
| WO | 00/60063 A1 | 10/2000 |
| WO | 02/070641 A1 | 9/2002 |
| WO | 2007/001261 A1 | 1/2007 |
| WO | 2007/001262 A1 | 1/2007 |
| WO | WO2007/001262 * | 1/2007 |
| WO | 2007/087242 A2 | 8/2007 |
| WO | WO2009155115 * | 12/2009 |
| WO | 2010/073000 A1 | 7/2010 |
| WO | WO-2012175401 A2 * | 12/2012 ......... C11D 3/38672 |

OTHER PUBLICATIONS

Fernandes et al. "Hydrolysis and synthesis reactions catalysed by Thermomyces lanuginosa lipase in the AOT/ISooctane reversed micellar system." pp. 1-7. Mar. 9, 2004.*

* cited by examiner

*Primary Examiner* — Gregory R Delcotto
*Assistant Examiner* — Preeti Kumar
(74) *Attorney, Agent, or Firm* — Eric Fechter

(57) ABSTRACT

Enzymes tend to be inactivated during wash by a bleach catalyst in combination with a source of organic peroxyacids. The risk of enzyme inactivation by active bleach catalyst is reduced when the release of the enzyme into the wash solution is delayed. The enzyme stability during washing together with a bleach catalyst can be improved by applying a delayed-release coating to cores which comprise the enzyme.

19 Claims, No Drawings

PARTICULATE COMPOSITION

CROSS-REFERENCE TO RELATED APPLICATIONS

This application is a 35 U.S.C. 371 national application of PCT/EP2012/061307 filed Jun. 14, 2012 which claims priority or the benefit under 35 U.S.C. 119 of European application no. 11170520.8 filed Jun. 20, 2011 and U.S. provisional application No. 61/498,763 filed Jun. 20, 2011 the contents of which are fully incorporated herein by reference.

FIELD OF THE INVENTION

The present invention relates to a particulate composition comprising:
a) particles comprising a source of organic peroxyacids, and
b) particles comprising a bleach catalyst, and
c) particles comprising an enzyme.

BACKGROUND OF THE INVENTION

Bleaching systems providing a source of organic peroxyacids are commonly included in particulate detergents to facilitate the removal of stains and soils. Examples include a combination of a hydrogen peroxide source such as perborate or percarbonate with a bleach activator such as TAED (tetraacetyl ethylene diamine) or NOBS (nonanoyloxybenzene sulphonate).

WO 2007/001261 and WO 2007/001262 disclose particulate detergents which contain particles comprising a source of organic peroxyacids, and particles comprising a bleach catalyst to improve the bleaching effect.

Enzymes are commonly used in particulate detergents to improve the removal of stains and soils. Examples are lipolytic enzymes (lipid esterases), particularly first-wash lipolytic enzymes (lipid esterases), e.g. variants of Lipolase™ (wild-type *Thermomyces lanuginosus* lipase) described in WO 97/07202 and WO 00/60063.

WO 9723606, WO 9528466, WO 9528468, and WO 9528469 disclose particulate compositions comprising delayed release enzyme granulates. GB 2 267 911 A, WO 02/070641 A1, EP 0 723 006 A2, WO 2010/073000 A1 and DE 10 2007 056166 A1 disclose particulate compositions comprising an enzyme.

SUMMARY OF THE INVENTION

The inventors have found that enzymes tend to be inactivated during wash by a bleach catalyst in combination with a source of organic peroxyacids. The inventors further found that the risk of enzyme inactivation is reduced when the release of the enzyme into the wash solution is delayed and that the enzyme stability during washing together with a bleach catalyst can be improved by applying a delayed-release coating to cores which comprise the enzyme.

Based on this insight, the inventors found that the enzyme stability during washing together with a bleach catalyst can be improved by applying a delayed-release coating to cores which comprise the enzyme.

Accordingly, the invention provides a particulate composition comprising:

a) particles comprising a source of organic peroxyacids, and
b) particles comprising a bleach catalyst, and
c) particles comprising
i) a core comprising an enzyme surrounded by
ii) a delayed-release coating.

In one aspect of the invention, the bleach catalyst is non-metal, and in another aspect the enzyme is a first-wash lipolytic enzyme (lipid esterase).

The invention also provides a method of preparing enzyme particles, comprising:
a) testing the bleach-catalyst sensitivity of at least one enzyme by determining the wash performance for a combination of the enzyme with a bleach catalyst and a source of organic peroxyacids, and comparing with the performance without the bleach catalyst, to identify a bleach-catalyst sensitive enzyme, and
b) providing a core comprising the sensitive enzyme, and surrounding the core with a delayed-release coating.

DETAILED DESCRIPTION OF THE INVENTION

Particulate Composition

The particulate composition comprises particles with an organic peroxyacid source, bleach catalyst particles and enzyme particles.

The particulate composition may be a detergent, e.g. a laundry detergent or a dish wash detergent, or it may be a premix for mixing with adjunct materials in the preparation of a detergent.

Source of Organic Peroxyacids

The particulate composition comprises a source of organic peroxyacids as a bleaching agent. The source of organic peroxyacids may be a preformed peracid or a diacyl peroxide, or it may comprise a source of hydrogen peroxide and a bleach activator.

In general, the compositions of the present invention may comprise from about 0.1% to about 50% or even from about 0.1% to about 25% bleaching agent by weight. The bleaching agent is a source of organic peroxyacids.

The organic peroxy acid source (peracid and/or bleach activator) is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The particles comprising the organic peroxyacids preferably have a release profile such that the time required to release 50% of the organic peroxyacids is below 100 seconds, particularly below 50 seconds or below 20 seconds. The test to determine whether these values are met is defined as Test Method 2: Dissolution test, below.

Pre-Formed Peracids:

Suitable preformed peracids include, but are not limited to, compounds selected from the group consisting of preformed peroxyacids or salts thereof, typically either a peroxycarboxylic acid or salt thereof, or a peroxysulphonic acid or salt thereof.

The pre-formed peroxyacid or salt thereof is preferably a peroxycarboxylic acid or salt thereof, typically having a chemical structure corresponding to the following chemical formula:

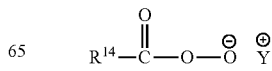

wherein: $R^{14}$ is selected from alkyl, aralkyl, cycloalkyl, aryl or heterocyclic groups; the $R^{14}$ group can be linear or branched, substituted or unsubstituted; and Y is any suitable counterion that achieves electric charge neutrality, preferably Y is selected from hydrogen, sodium or potassium. Preferably, $R^{14}$ is a linear or branched, substituted or unsubstituted $C_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Preferably, the peroxyacid or salt thereof has a melting point in the range of from 30° C. to 60° C.

The pre-formed peroxyacid or salt thereof can also be a peroxysulphonic acid or salt thereof, typically having a chemical structure corresponding to the following chemical formula:

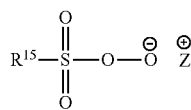

wherein: $R^{15}$ is selected from alkyl, aralkyl, cycloalkyl, aryl or heterocyclic groups; the $R^{15}$ group can be linear or branched, substituted or unsubstituted; and Z is any suitable counterion that achieves electric charge neutrality, preferably Z is selected from hydrogen, sodium or potassium. Preferably $R^{15}$ is a linear or branched, substituted or unsubstituted $C_{6-9}$ alkyl.

Sources of Hydrogen Peroxide

Examples are inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and Bleach Activators Bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof.

Diacyl Peroxides

The diacyl peroxide (DAP) bleaching species is preferably selected from diacyl peroxides of the general formula:

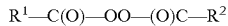

in which $R^1$ represents a $C_6$-$C_{18}$ alkyl, preferably $C_6$-$C_{12}$ alkyl group containing a linear chain of at least 5 carbon atoms and optionally containing one or more substituents (e.g. —N$^+$(CH$_3$)$_3$, —COOH or —CN) and/or one or more interrupting moieties (e.g. —CONH— or —CH=CH—) interpolated between adjacent carbon atoms of the alkyl radical, and $R^2$ represents an aliphatic group compatible with a peroxide moiety, such that $R^1$ and $R^2$ together contain a total of 8 to 30 carbon atoms. In one preferred aspect $R^1$ and $R^2$ are linear unsubstituted $C_6$-$C_{12}$ alkyl chains. Most preferably $R^1$ and $R^2$ are identical. Diacyl peroxides, in which both $R^1$ and $R^2$ are $C_6$-$C_{12}$ alkyl groups, are particularly preferred. Preferably, at least one of, most preferably only one of, the R groups ($R_1$ or $R_2$), does not contain branching or pendant rings in the alpha position, or preferably neither in the alpha nor beta positions or most preferably in none of the alpha or beta or gamma positions. In one further preferred embodiment the DAP may be asymmetric, such that preferably the hydrolysis of R1 acyl group is rapid to generate peracid, but the hydrolysis of R2 acyl group is slow.

The tetraacyl peroxide bleaching species is preferably selected from tetraacyl peroxides of the general formula:

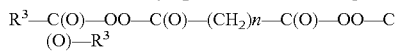

in which $R^3$ represents a $C_1$-$C_9$ alkyl, preferably $C_3$-$C_7$, group and n represents an integer from 2 to 12, preferably 4 to 10 inclusive.

Preferably, the diacyl and/or tetraacyl peroxide bleaching species is present in an amount sufficient to provide at least 0.5 ppm, more preferably at least 10 ppm, and even more preferably at least 50 ppm by weight of the wash liquor. In a preferred embodiment, the bleaching species is present in an amount sufficient to provide from about 0.5 to about 300 ppm, more preferably from about 30 to about 150 ppm by weight of the wash liquor.

Bleach Catalyst

Bleach Catalysts may be provided by: non-metal bleach catalysts, catalytic metal complexes or ligands which form catalytic metal complexes. The bleach catalyst is typically used in an amount which provides 0.001-0.02 g of active material per 1 of wash liquor.

Non-Metal Bleach Catalysts

The bleach catalyst is capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Suitable iminium cations and polyions include, but are not limited to, N-methyl-3,4-dihydroisoquinolinium tetrafluoroborate, prepared as described in Tetrahedron (1992), 49(2), 423-38 (see, for example, compound 4, p. 433); N-methyl-3,4-dihydroisoquinolinium p-toluene sulphonate, prepared as described in U.S. Pat. No. 5,360,569 (see, for example, Column 11, Example 1); and N-octyl-3,4-dihydroisoquinolinium p-toluene sulphonate, prepared as described in U.S. Pat. No. 5,360,568 (see, for example, Column 10, Example 3).

Suitable iminium zwitterions include, but are not limited to, N-(3-sulfopropyl)-3,4-dihydroisoquinolinium, inner salt, prepared as described in U.S. Pat. No. 5,576,282 (see, for example, Column 31, Example II); N-[2-(sulphooxy)dodecyl]-3,4-dihydroisoquinolinium, inner salt, prepared as described in U.S. Pat. No. 5,817,614 (see, for example, Column 32, Example V); 2-[3-[(2-ethylhexyl)oxy]-2-(sulphooxy)propyl]-3,4-dihydroisoquinolinium, inner salt, prepared as described in WO05/047264 (see, for example, page 18, Example 8), and 2-[3-[(2-butyloctyl)oxy]-2-(sulphooxy)propyl]-3,4-dihydroisoquinolinium, inner salt.

Suitable modified amine oxygen transfer catalysts include, but are not limited to, 1,2,3,4-tetrahydro-2-methyl-1-isoquinolinol, which can be made according to the procedures described in Tetrahedron Letters (1987), 28(48), 6061-6064. Suitable modified amine oxide oxygen transfer catalysts include, but are not limited to, sodium 1-hydroxy-N-oxy-N-[2-(sulphooxy)decyl]-1,2,3,4-tetrahydroisoquinoline.

Suitable N-sulphonyl imine oxygen transfer catalysts include, but are not limited to, 3-methyl-1,2-benzisothiazole 1,1-dioxide, prepared according to the procedure described in the Journal of Organic Chemistry (1990), 55(4), 1254-61.

Suitable N-phosphonyl imine oxygen transfer catalysts include, but are not limited to, [R-(E)]-N-[(2-chloro-5-nitrophenyl)methylene]-P-phenyl-P-(2,4,6-trimethylphenyl)-phosphinic amide, which can be made according to the procedures described in the Journal of the Chemical Society, Chemical Communications (1994), (22), 2569-70.

Suitable N-acyl imine oxygen transfer catalysts include, but are not limited to, [N(E)]-N-(phenylmethylene)acetamide, which can be made according to the procedures described in Polish Journal of Chemistry (2003), 77(5), 577-590.

Suitable thiadiazole dioxide oxygen transfer catalysts include but are not limited to, 3-methyl-4-phenyl-1,2,5-thiadiazole 1,1-dioxide, which can be made according to the procedures described in U.S. Pat. No. 5,753,599 (Column 9, Example 2).

Suitable perfluoroimine oxygen transfer catalysts include, but are not limited to, (Z)-2,2,3,3,4,4,4-heptafluoro-N-(nonafluorobutyl)butanimidoyl fluoride, which can be made according to the procedures described in Tetrahedron Letters (1994), 35(34), 6329-30.

Suitable cyclic sugar ketone oxygen transfer catalysts include, but are not limited to, 1,2:4,5-di-O-isopropylidene-D-erythro-2,3-hexodiuro-2,6-pyranose as prepared in U.S. Pat. No. 6,649,085 (Column 12, Example 1).

Preferably, the bleach catalyst comprises an iminium and/or carbonyl functional group and is typically capable of forming an oxaziridinium and/or dioxirane functional group upon acceptance of an oxygen atom, especially upon acceptance of an oxygen atom from a peroxyacid and/or salt thereof. Preferably, the bleach catalyst comprises an oxaziridinium functional group and/or is capable of forming an oxaziridinium functional group upon acceptance of an oxygen atom, especially upon acceptance of an oxygen atom from a peroxyacid and/or salt thereof. Preferably, the bleach catalyst comprises a cyclic iminium functional group, preferably wherein the cyclic moiety has a ring size of from five to eight atoms (including the nitrogen atom), preferably six atoms. Preferably, the bleach catalyst comprises an aryliminium functional group, preferably a bi-cyclic aryliminium functional group, preferably a 3,4-dihydroisoquinolinium functional group. Typically, the imine functional group is a quaternary imine functional group and is typically capable of forming a quaternary oxaziridinium functional group upon acceptance of an oxygen atom, especially upon acceptance of an oxygen atom from a peroxyacid and/or salt thereof.

Preferably, the bleach catalyst has a chemical structure corresponding to the following chemical formula

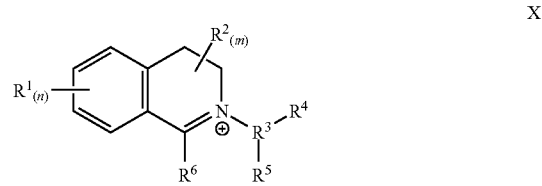

wherein: n and m are independently from 0 to 4, preferably n and m are both 0; each $R^1$ is independently selected from a substituted or unsubstituted radical selected from the group consisting of hydrogen, alkyl, cycloalkyl, aryl, fused aryl, heterocyclic ring, fused heterocyclic ring, nitro, halo, cyano, sulphonato, alkoxy, keto, carboxylic, and carboalkoxy radicals; and any two vicinal $R^1$ substituents may combine to form a fused aryl, fused carbocyclic or fused heterocyclic ring; each $R^2$ is independently selected from a substituted or unsubstituted radical independently selected from the group consisting of hydrogen, hydroxy, alkyl, cycloalkyl, alkaryl, aryl, aralkyl, alkylenes, heterocyclic ring, alkoxys, arylcarbonyl groups, carboxyalkyl groups and amide groups; any $R^2$ may be joined together with any other of $R^2$ to form part of a common ring; any geminal $R^2$ may combine to form a carbonyl; and any two $R^2$ may combine to form a substituted or unsubstituted fused unsaturated moiety; $R^3$ is a $C_1$ to $C_{20}$ substituted or unsubstituted alkyl; $R^4$ is hydrogen or the moiety $Q_t$-A, wherein: Q is a branched or unbranched alkylene, t=0 or 1 and A is an anionic group selected from the group consisting of $OSO_3^-$, $SO_3^-$, $CO_2^-$, $OCO_2^-$, $OPO_3^{2-}$, $OPO_3H^-$ and $OPO_2^-$; $R^5$ is hydrogen or the moiety $—CR^{11}R^{12}—Y-G_b-Y_c—[(CR^9R^{10})_y—O]_k—R^8$, wherein: each Y is independently selected from the group consisting of O, S, N—H, or NW; and each $R^8$ is independently selected from the group consisting of alkyl, aryl and heteroaryl, said moieties being substituted or unsubstituted, and whether substituted or unsubstituted said moieties having less than 21 carbons; each G is independently selected from the group consisting of CO, $SO_2$, SO, PO and $PO_2$; $R^9$ and $R^{19}$ are independently selected from the group consisting of H and $C_1$-$C_4$ alkyl; $R^{11}$ and $R^{12}$ are independently selected from the group consisting of H and alkyl, or when taken together may join to form a carbonyl; b=0 or 1; c can =0 or 1, but c must =0 if b=0; y is an integer from 1 to 6; k is an integer from 0 to 20; $R^6$ is H, or an alkyl, aryl or heteroaryl moiety; said moieties being substituted or unsubstituted; and X, if present, is a suitable charge balancing counterion, preferably X is present when $R^4$ is hydrogen, suitable X, include but are not limited to: chloride, bromide, sulphate, methosulphate, sulphonate, p-toluenesulphonate, borontetrafluoride and phosphate.

A preferred bleach catalyst has a structure corresponding to general formula below:

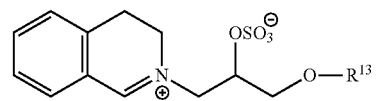

wherein $R^{13}$ is a branched alkyl group containing from three to 24 carbon atoms (including the branching carbon atoms) or a linear alkyl group containing from one to 24 carbon atoms; preferably $R^{13}$ is a branched alkyl group containing from eight to 18 carbon atoms or linear alkyl group containing from eight to eighteen carbon atoms; preferably $R^{13}$ is selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl; preferably $R^{13}$ is selected from the group consisting of 2-butyloctyl, 2-pentylnonyl, 2-hexyldecyl, iso-tridecyl and iso-pentadecyl.

The bleach catalyst may be one described in WO 2007/001261 or WO 2007/001262, e.g. having formula (1) of WO 2007/001262 with $R^1$=2-butyl-octyl.

Catalytic Metal Complexes

Suitable catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936; 5,595,967. Such cobalt catalysts are readily prepared by known procedures, such as taught for example in U.S. Pat. Nos. 5,597,936, and 5,595,967.

Compositions herein may also suitably include a transition metal complex of ligands such as bispidones (U.S. Pat. No. 7,501,389) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in U.S. Pat. No. 6,225,464.

Liquids which Form Catalytic Metal Complexes

Particularly ligands such as those described above, which form a complex with a transition metal. Formation of such catalytic metal complexes from suitable ligands is described, for example in EP1109965, EP1259522, EP 1240378 and EP 1240379.

Enzyme

The enzyme may in particular be an enzyme which is sensitive to the bleach catalyst. The enzyme may be an amylase, a carbohydrase, a protease, a lipolytic enzyme, a cellulase, an oxidoreductase, a mannanase or a pectate lyase.

Preferably the enzyme is present in the composition in amounts from 0.00001% to 2%, more preferably from to 0.0001% to 0.02%, most preferably from 0.001% to 0.01%.

Lipolytic Enzyme

The lipolytic enzyme (or lipid esterase) is an enzyme in class EC 3.1.1 as defined by Enzyme Nomenclature. It may have lipase activity (triacylglycerol lipase, EC 3.1.1.3), cutinase activity (EC 3.1.1.74), sterol esterase (EC 3.1.1.13), and/or wax-ester hydrolase activity (EC 3.1.1.50).

The lipolytic enzyme may in particular be a lipase with first-wash activity as described in WO9707202 and WO 00/60063. A suitable protocol for determining whether a triacylglycerol lipase exhibits first wash activity is given in Test Method 1. Suitable triacylglycerol lipases exhibiting first wash activity can be selected from variants of the *Thermomyces lanuginosus* (*Humicola lanuginosa*) lipase, such as Lipex™, Lipolex™ and Lipoclean,™ all products of Novozymes, Bagsvaerd, Denmark. Preferred first wash lipases are described in WO0060063 and WO2006/090335, most preferably the first wash lipase is selected from *Thermomyces lanuginosus* lipase variants with mutations T231R and N233R.

The lipase may be selected among *Thermomyces lanuginosus* lipase (TLL, shown as SEQ ID NO: 2 in WO 2009/109500), *Alcaligenes* sp. lipase, *Achromobacter* sp. lipase, *Burkholderia cepacia* lipase, *Pseudomonas* lipases, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), *Bacillus* lipases, e.g., from *B. subtilis* (Dartois et al. (1993), Biochemica et Biophysica Acta, 1131, 253-360), *B. stearothermophilus* (JP 64/744992) or *B. pumilus* (WO 91/16422), or it may be a variant which has an amino sequence with at least 80% identity to one of these, particularly at least 85%, at least 90%, at least 95% or at least 98% identity.

Examples of TLL variants are described in WO 1992/005249, Lipolase Ultra), WO0060063, WO9707202, WO0032758, WO02055679, WO04099400, WO07087508 and WO 2009/109500. Commercial lipases include the following products of Novozymes NS: Novozym™ 435, Novozym 735, Lipozyme™ RM, Novozym 388, Lipolase Ultra™, Lipex™, Lipoprime™, Lipolase™, Lipoclean™ and Lipolex™.

Suitable cutinases may be derived from a strain of *Aspergillus*, in particular *Aspergillus oryzae*, a strain of *Alternaria*, in particular *Alternaria brassiciola*, a strain of *Fusarium*, in particular *Fusarium solani*, *Fusarium solani pisi*, *Fusarium oxysporum*, *Fusarium oxysporum cepa*, *Fusarium roseum culmorum*, or *Fusarium roseum sambucium*, a strain of *Helminthosporum*, in particular *Helminthosporum sativum*, a strain of *Humicola*, in particular *Humicola insolens*, a strain of *Pseudomonas*, in particular *Pseudomonas mendocina*, or *Pseudomonas putida*, a strain of *Rhizoctonia*, in particular *Rhizoctonia solani*, a strain of *Streptomyces*, in particular *Streptomyces scabies*, a strain of *Coprinopsis*, in particular *Coprinopsis cinerea*, a strain of *Thermobifida*, in particular *Thermobifida fusca*, a strain of *Magnaporthe*, in particular *Magnaporthe grisea*, or a strain of *Ulocladium*, in particular *Ulocladium consortiale*.

In a preferred embodiment, the cutinase is selected from variants of the *Pseudomonas mendocina* cutinase described in WO 2003/076580 (Genencor), such as the variant with three substitutions at I178M, F180V, and S205G.

In another preferred embodiment, the cutinase is a wild-type or variant of the six cutinases endogenous to *Coprinopsis cinerea* described in H. Kontkanen et al, App. Environ. Microbiology, 2009, p 2148-2157

In another preferred embodiment, the cutinase is a wild-type or variant of the two cutinases endogenous to *Trichoderma reesei* described in WO2009007510 (VTT).

In a most preferred embodiment the cutinase is derived from a strain of *Humicola insolens*, in particular the strain *Humicola insolens* DSM 1800. *Humicola insolens* cutinase is described in WO 96/13580 which is hereby incorporated by reference. The cutinase may be a variant, such as one of the variants disclosed in WO 00/34450 and WO 01/92502. Preferred cutinase variants include variants listed in Example 2 of WO 01/92502. Preferred commercial cutinases include Novozym 51032 (available from Novozymes, Bagsvaerd, Denmark).

Suitable sterol esterases may be derived from a strain of *Ophiostoma*, for example *Ophiostoma piceae*, a strain of *Pseudomonas*, for example *Pseudomonas aeruginosa*, or a strain of *Melanocarpus*, for example *Melanocarpus albomyces*.

In a most preferred embodiment the sterol esterase is the *Melanocarpus albomyces* sterol esterase described in H. Kontkanen et al, Enzyme Microb Technol., 39, (2006), 265-273.

Suitable wax-ester hydrolases may be derived from *Simmondsia chinensis*.

Amylase

The amylase may be an □-amylase obtained from *Bacillus*, e.g. *B. subtilis* and *B. licheniformis*, in particular the amylase from a special strain of *B. licheniformis*, described in more detail in GB 1,296,839.

Examples of useful amylases are described in WO 94/02597, WO 94/18314, WO 1995/010603, WO 1995/026397, WO 96/23873, WO 97/43424, and WO 00/60060, WO 2001/066712, WO 2006/002643, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

In a particular embodiment the alpha-amylase is derived from *Bacillus* sp. strains NCIB 12289, NCIB 12512, NCIB 12513 and DSM 9375. Especially preferred are the alpha-amylases shown in SEQ ID NOS 1 and 2 of WO 95/26397.

Commercially available amylases are NATALASE™, STAINZYME™, STAINZYME PLUS™, TERMAMYL™ ULTRA, DURAMYL™, TERMAMYL™, FUNGAMYL™ and BAN™ (Novozymes A/S), RAPIDASET™, PURASTAR™ and PURASTAR OXAM™ (from Genencor International Inc.).

Protease

Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™ Primase™, Duralase™, Esperase™, and Kannase™ (Novozymes a/S), Maxatase™, Maxacal™ Maxapem™, Properase™, Purafect™, Purafect OxP™, FN2™, and FN3™ (Genencor International Inc.).

Cellulase

Suitable cellulases include complete cellulases or mono-component endoglucanases of bacterial or fungal origin. Chemically or genetically modified mutants are included. The cellulase may for example be a mono-component or a mixture of mono-component endo-1,4-beta-glucanase often just termed endoglucanases (EC 3.2.1.4). Some xyloglucanases may also have endoglucanase activity and are also considered as suitable cellulases in the present invention. Suitable cellulases are disclosed in U.S. Pat. No. 4,435,307, which discloses fungal cellulases produced from *Humicola insolens*. Especially suitable cellulases are the cellulases having textile care benefits. Examples of such cellulases are cellulases described in European patent application No. 0 495 257.

Suitable mono-component endoglucanases may be obtained from one or more of the following species *Exidia glandulosa, Crinipellis scabella, Fomes fomentarius, Spongipellis* sp., *Rhizophlyctis rosea, Rhizomucor pusillus, Phycomyces nitens,* and *Chaetostylum fresenii, Diplodia gossypina, Microsphaeropsis* sp., *Ulospora bilgramii, Aureobasidium* sp., *Macrophomina phaseolina, Ascobolus stictoides, Saccobolus dilutellus, Peziza, Penicillium verruculosum, Penicillium chrysogenum,* and *Thermomyces verrucosus, Trichoderma reesei* aka *Hypocrea jecorina, Diaporthe syngenesia, Colletotrichum lagenarium, Xylaria hypoxylon, Nigrospora* sp., *Nodulisporum* sp., and *Poronia punctata, Cylindrocarpon* sp., *Nectria pinea, Volutella colletotrichoides, Sordaria fimicola, Sordaria macrospora, Thielavia thermophila, Syspastospora boninensis, Cladorrhinum foecundissimum, Chaetomium murorum, Chaetomium virescens, Chaetomium brasiliensis, Chaetomium cunicolorum, Myceliophthora thermophila, Gliocladium catenulatum, Scytalidium thermophila, Acremonium* sp *Fusarium solani, Fusarium anguioides, Fusarium poae, Fusarium oxysporum* ssp. *lycopersici, Fusarium oxysporum* ssp. *passiflora, Humicola nigrescens, Humicola grisea, Fusarium oxysporum, Thielavia terrestris* or *Humicola insolens*. One preferred endoglucanase is disclosed in WO 96/29397 as SEQ ID NO: 9 (hereby incorporated by reference) or an enzyme with at least 70% identity thereto and variants thereof as disclosed in Example 1 of WO 98/12307. Another preferred endoglucanase is disclosed in WO 91/017243 (SEQ ID NO:2) or endoglucanases variants as disclosed in WO 94/007998.

Endoglucanases with an anti-redeposition effect may be obtained from fungal endoglucanases lacking a carbohydrate-binding module (CBM) from a number of bacterial sources. Some sources are *Humicola insolens, Bacillus* sp. deposited as DSM 12648, *Bacillus* sp. KSMS237 deposited as FERM P-16067, *Panibacillus polymyxa*, and *Panibacillus pabuli*. Specific anti-redeposition endoglucanase are disclosed in WO 91/17244 (FIG. 14) (hereby incorporated by reference), WO 2002/099091 position 1-773 of SEQ ID NO: 2 (hereby incorporated by reference), WO 04/053039 SEQ ID NO: 2 (hereby incorporated by reference), JP 2000210081 position 1 to 824 of SEQ ID NO: 1 (hereby incorporated by reference).

Xyloglucanases with an anti-redeposition effect may be obtained from a number of bacterial sources. Some sources are *Bacillus licheniformis, Bacillus agaradhaerens*, (WO 99/02663) *Panibacillus polymyxa*, and *Panibacillus pabuli* (WO01/62903). Suitable variants of xyloglucasnes are also described in PCT/EP2009/056875. A commercially available xyloglucanase is Whitezyme® (Novozymes NS).

Commercially available cellulases include Celluclast® produced from *Trichoderma reesei*, Celluzyme® produced from *Humicola insolens*. Commercially available endoglucanases are Carezyme®, Renozyme®, Endolase® and Celluclean® (Novozymes NS), and KAC-500(B)™ (Kao Corporation) and Clazinase™, Puradax™ EG L and Puradax HA (Danisco A/S).

Pectate Lyase

The pectate lyase may be a wild-type enzymes derived from *Bacillus*, particularly *B. lichemiformis* or *B. agaradhaerens*, or a variant derived of these, e.g. as described in U.S. Pat. No. 6,124,127, WO 1999/027083, WO 1999/027084, WO 2002/006442, WO 2002/092741, or WO 2003/095638.

Mannanase

The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619.

Sensitivity of Enzyme to Bleach Catalyst

The delayed-release coating is particularly applicable to protection of an enzyme which is sensitive to a bleach catalyst. The sensitivity is determined by testing the wash performance of the enzyme on fatty soiling in a detergent containing the bleach catalyst and a source of organic peracids, and comparing with the performance in a similar detergent without the bleach catalyst. The enzyme is considered sensitive if the ratio of wash performance without and with bleach activator is more than 2, particularly more than 5.

Enzyme-Containing Core

The core comprises the enzyme and may also include binders (such as synthetic polymer, wax, fat, or carbohydrate). The core may further include additional materials such as fillers, fibre materials (cellulose or synthetic fibres), stabilizing agents, solubilising agents, suspension agents, viscosity regulating agents, light spheres, plasticizers, salts, lubricants and fragrances.

The core can be prepared by granulation, e.g. by use of granulation techniques including: crystallisation, precipitation, pan-coating, fluid bed coating, fluid bed agglomeration, rotary atomization, extrusion, prilling, spheronization, size reduction methods, drum granulation, and/or high shear granulation.

The core may consist of an inert particle with the enzyme absorbed into it, or with the enzyme applied on to the surface e.g. via fluid bed coating.

The core particle may have a diameter of 20-2000 μm, particularly 50-1500 μm, 100-1500 μm or 250-1200 μm.

Coating

The granules have a delayed-release coating which may comprise a hydrophobic substance, e.g. a high-melting wax or fat, particularly in an amount of 1-50% or 5-15% by weight. The coating may further comprise a water-insoluble substance, e.g. kaolin, talc or calcium carbonate, e.g. in an amount of 60-75% by weight. The coating may constitute 15-35% by weight of the coated particle. The coating may be as described in WO 92/12645 or WO 97/16076.

The delayed-release coating may comprise a substrate for the enzyme. As an example, the enzyme may be a lipolytic enzyme, and the coating may comprise lipids, mono-, di- and triglycerides such as tripalmitin, palm oil, beeswax, jojoba oil, carnauba wax, carnauba wax, polyesters, polyester block copolymers such as polyethylene terephthalate/polyoxyethylene terephthalate (PET/POET) block copolymers and polycaprolactone, preferably comprising palm oil.

The release profile for the enzyme in the granules is preferably such that the time required to release 50% of the enzyme activity is at least 100 seconds, at least 200 seconds or at least 300 seconds. The time required to release 50% or 90% of the enzyme activity for the coated granules is preferably at least 1.5 times, at least 2 times or at least 3 times longer than the time required for similar enzyme granules without a delayed-release coating. The test to determine whether these values are met is defined as Test Method 2: Dissolution test, below.

In addition to the delayed-release coating, the granules may optionally comprise one or more additional coatings, either as an undercoat or a topcoat, e.g. to reduce dust formation. Such a coating may comprise polyethylene glycol (PEG), polyvinyl alcohol (PVA) or hydroxypropyl methyl cellulose (HPMC).

Detergent Composition

The granules are particularly suited for incorporation in a granular detergent composition comprising a surfactant. Enzyme granules according to the invention result in improved storage stability of the enzyme when the granules are incorporated in a detergent, even a detergent comprising aggressive components such as a bleaching system.

The detergent composition may for example be formulated as a laundry detergent composition for hand or machine washings including a cleaning additive composition suitable for pre-treatment of stained fabrics or a fabric softener composition, or a detergent composition for use in general household hard surface cleaning operations, or a composition for hand or machine dishwashing operations.

The detergent composition of the invention may be in any convenient dry form, e.g., a bar, a tablet, a powder, a granulate or a paste. It may also be a liquid detergent, either an aqueous or non-aqueous liquid detergent.

Surfactant

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfosuccinic acid or soap, and combinations thereof.

Non-limiting examples of cationic surfactants include alklydimethylehanolamine quat (ADMEAQ), cetyltrimethylammonium bromide (CTAB), dimethyldistearylammonium chloride (DSDMAC), and alkylbenzyldimethylammonium, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkyl-polyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

Non-limiting examples of zwitterionic surfactants include betaine, alkyldimethylbetaine, and sulfobetaine, and combinations thereof.

Builder or Complexing Agent

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

In a dish wash detergent, the level of builder is typically 40-65%, particularly 50-65%. The builder and/or co-builder may particularly be a chelating agent that forms water-soluble complexes with Ca and Mg. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2''-nitrilotriethanol (TEA), and carboxymethylinulin (CMI), and combinations thereof.

The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2''-nitrilotriacetic acid (NTA), ethylene-diaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diylbis(phosphonic acid) (HEDP), ethylenediamine-tetrakis (methylene)tetrakis(phosphonic acid) (EDTMPA), diethylenetriamine-pentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N, N-diacetic acid (ISDA), phenylalanine-N,N-diacetic acid (PHDA), anthranilic acid-N,N-diacetic acid (ANDA), sulfanilic acid-N, N-diacetic acid (SLDA), taurine-N, N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta(Methylene Phosphonic acid) (DTPMP), amino-tris (methylenephosphonic acid) (ATMP), and combinations and salts thereof. Further exemplary builders and/or co-builders are described in, e.g., WO 09/102854, U.S. Pat. No. 5,977,053.

Polymer

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs, as found for surfactants and lipids forming miceller, lamellar or other well defined meso-phases. Instead, many hydrotropes show a continuous-type aggregation process where the size of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Non-limiting examples of hydrotropes include sodium benzene sulfonate, sodium p-toluene sulfonates (STS), sodium xylene sulfonates (SXS), sodium cumene sulfonates (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Fabric Hueing Agents

The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257, WO2007/087243.

Detergent Formulations

The enzyme granules may be included in a granular detergent formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, WO09/015951, WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905, WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792, WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, or WO2010000636.

Test Methods

Test Method 1: First Wash Lipase Test

Lard First Wash Test

Whether any specific lipase enzyme gives better First Wash lard removal performance than WT Lipolase (from Novozymes, described in U.S. Pat. No. 5,869,438, SEQ ID:2), can be determined by comparing the performance results of WT Lipolase with the performance results of the specific lipase enzyme according to the following test:

The wash performance of lipolytic enzymes is tested in a one cycle wash trial carried out in a thermostated Terg-O-tometer (TOM) followed by line-drying. The experimental conditions are as follows:

Wash liquor: 1000 ml per beaker

Swatches: 7 flat cotton swatches (9×9 cm) (supplied by Warwick-Equest) per beaker Stain: Lard coloured red with sudan red dye (Sigma) (0.75 mg Sudan red/g lard). 50 µl of lard/sudan red heated to 70° C. are applied to the centre of each swatch. After application of the stain the swatches are heated in an oven for 25 minutes at 75° C. and then stored overnight at room temperature.

Water for preparing wash liquor: 3.2 mM $Ca^{2+}/Mg^{2+}$ (in a ratio of 5:1)

Detergent: 5 g/l of detergent composition A.

Detergent Composition A:

0.300 g/l alkyl sulphate (AS; $C_{14-16}$)

0.650 g/l of alcohol ethoxylate (AEO; $C_{12-14}$, 6EO)

1.750 g/l Zeolite P 0.145 g/l $Na_2CO_3$ 0.020 g/l Sokalan CP5 (BASF)

0.050 g/l CMC (carboxy methyl cellulose—Finnfix BDA ex CP Kelco)

5 g/l of detergent composition A are mixed into deionised water with added hardness (3.2 mM $Ca^{2+}/Mg^{2+}$ (5:1)) and the pH artificially adjusted to pH 10.2 by adding NaOH. Lipase enzyme is added.

Concentration of lipolytic enzyme: 0 and 12500 LU/l

Wash time: 20 minutes

Wash temperature: 30° C.

Rinse: 15 minutes in running tap water

Drying: overnight at room conditions (approx. 20° C., 30-40% RH).

Evaluation: the reflectance was measured at 460 nm.

The percentage of lard removed is determined as:
Delta reflectance (dR) defined as:
(R(Swatches washed in detergent with lipase)−R (Swatches washed in detergent without lipase)

The reflectance (which may also be termed remission) is measured on an Elrepho 2000 apparatus from Datacolor which illuminates the sample with 2 xenon blitz lamps and measures the amount of reflected light so that entirely white corresponds to a 100% reflectance and entirely black a 0% reflectance. Comparing the results for lard removal due to the presence of enzyme, lipase enzymes giving better performance than WT Lipolase™ are suitable for use in the compositions of the present invention.

Test Method 2: Dissolution Test

A detergent solution is prepared according to test detergent description in Example 2 in 18 dH water. The detergent solution is stirred for 30 min and filtered through a sheet of gauze. The detergent solution is adjusted to 20° C.±2° C. and placed under a 4-bladed propeller stirrer adjusted to 600 rpm±10 rpm. 75 mg enzyme containing particle/l detergent solution is added at $T_0$. After addition of the enzyme containing particles the concentration of the enzyme released to the detergent solution is measured every 15 seconds for the first 60 seconds by withdrawing samples from the detergent solution. Subsequently samples are taken out every 30 seconds until 120 seconds and every 60 seconds until 1100 seconds. The enzyme activity in the withdrawn samples are measured in a suitable analytical method, e.g. for a lipase enzyme by use of assays involving synthetic substrates such as p-nitrophenyl butyrate or p-nitrophenyl palmitate. The time for 50% resp. 90% release of the enzyme from the enzyme containing particles are calculated.

The same method is applied to organic peroxyacid source particles to determine the time for 50% resp. 90% release of the organic peroxyacid source.

EXAMPLES

Example 1: Preparation of Lipase Granules with Delayed-Release Coating

A coated lipase was prepared as follows. The lipase was Lipex™ (product of Novozymes NS, described in WO 00/60063). It was formulated as a T-granulate produced essentially as in example 1 of WO 2004/003188 (Intl Appl. No. PCT/DK03/000456) (containing enzyme, Na-sulfate, cellulose fibers, calcium carbonate and a binder, e.g. sucrose or dextrin). This was coated with a coating consisting of 31% of palm oil, 50% of kaolin or calcium carbonate and 19% of titanium dioxide (% by weight). The amount of the coating material made up 25% by weight of the coated granules.

| Ingredient | In core (wt %) | In outer coating (wt %) | Total (wt %) |
| --- | --- | --- | --- |
| Sodium sulfate | 67 | | 49 |
| Kaolin | 9 | 50 | 19 |
| Cellulose | 10 | | 8 |
| Dextrin | 3 | | 2 |
| Sucrose | 2 | | 2 |
| Lipase (and other dry matter from concentrate) | 9 | | 7 |
| Palm oil | | 31 | 8 |
| Titanium dioxide | | 19 | 5 |

Example 2: Washing Tests with Coated Lipase and Organic Catalyst

The wash performance and the resistance to organic catalyst of the coated lipase were tested in washing tests with a model detergent (described below) using textile swatches soiled with various fatty stains (also described below).

The invention formulation was the coated lipase granulate prepared in Example 1. For comparison, the same lipase in the form of a conventional granulate coated with PEG (polyethylene glycol) was used as a conventional formulation. The organic non-metal bleach catalyst was a compound according to Formula 1 in WO 2007/001262 with $R^1$=2-butyl-octyl.

Experimental Conditions

| | | | | |
| --- | --- | --- | --- | --- |
| Machine | Miele Softtronic W2245 (EU) | | | |
| Program | Minimum Iron, Water Plus, approx 15 L water | | | |
| Temperature | 30° C. | | | |
| Water hardness | Water hardness Wash: 18dH (molar ratio between $Ca^{2+}/Mg^{2+}/HCO3^-$ 4:1:7.5) | | | |
| Test detergent | LAS | 0.9 g/l | | |
| | AEO | 0.2 g/l | | |
| | Na2CO3 | 0.53 g/l | | |
| | Zeolite A4 | 1.07 g/l | | |
| | Na3citrate | 0.52 g/l | | |
| | Percarbonate | 1 g/l | | |
| | TAED | 0.25 g/l | | |
| | Bleach catalyst | −/+125 mg/l (2.5 ppm active) | | |
| pH | As is | | | |
| Swatches/test material | 2 of each of the below stains attached to tea-towels in 3 corners | | | |
| | Substrate | Product code | Manufacturer | Measurements |
| | Mustard | CS67 (4 × 9 cm) | CFT | Color eye, Reflectance, 540 nm |
| | Hamburger grease | 10 × 10 cm blue knitted cotton, Stain diameter 5 cm | Equest | Scanner, Intensity |
| | Lard | | | |
| | Margarine | | | |
| | Bacon grease | | | |
| | Butter | | | |

| | Drying | Lying flat on blotting paper, 24 h, room temperature, in dark |
|---|---|---|
| | Ballast | 2.7 kg cotton ballast |
| | Enzymes | Dosage 0.25 mg enzyme protein (EP)/l |
| | Repetitions | 3 repeated washes per condition |

Wash Performance Evaluation of Blue Equest Stains

The wash performance of the blue Equest stains is measured after 24 hours+/−2 hours of drying as the brightness of the color of the textile washed. Brightness can also be expressed as the intensity of the light reflected from the sample when illuminated with white light. When the sample is stained the intensity of the reflected light is lower than that of a clean sample. Therefore the intensity of the reflected light can be used to measure wash performance.

Color measurements are made with a professional flatbed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The scans are made with a resolution of 200 dpi.

The intensity value (Int) is calculated by adding the RGB values together as vectors and then taking the length of the resulting vector:

$$Int = \sqrt{r^2 + g^2 + b^2}.$$

The wash performance (P) of the lipase formulation is calculated in accordance with the below formula:

$$P = \Delta Int = Int(v) - Int(r)$$

where

Int(v) is the light intensity value of textile surface washed with the lipase formulation, and Int(r) is the light intensity value of textile surface washed without the lipase formulation.

Wash Performance Evaluation of CS67

Wash performance is expressed as a delta remission value (ΔRem). Light reflectance evaluations of the swatches were done after 24 hours of drying using a Macbeth Color Eye 7000 reflectance spectrophotometer with very small aperture. The measurements were made without UV in the incident light and remission at 540 nm was extracted. Measurements were made on washed swatches. The test swatch to be measured was placed on top of another swatch of same type and color (twin swatch).

$$P = \Delta REM = Rem(v) - Rem(r)$$

where

Rem(v) is the light intensity value of textile surface washed with the lipase formulation, and Rem(r) is the light intensity value of textile surface washed without the lipase formulation.

Calculation of Relative Performance Score

A relative performance score is given as the result of the full scale was washed in accordance with the definition:

Relative Performance scores (RP) give performance (P) of the tested lipase formulation against the conventional lipase formulation:

$$RP = P(\text{invention formulation}) / P(\text{conventional formulation}).$$

RPavg indicates the average relative performance compared to the conventional lipase formulation on each swatch type at all repetitions (3 repeated washes with 2 stains in each wash)

A lipase formulation is considered to exhibit improved wash performance, if it performs better than the conventional lipase formulation.

The resistance of the lipase formulation against the bleach catalyst is calculated in accordance with the below formulation Calculation of Residual Performance Score (ResP)

Residual performance score (ResP) is calculated as the performance (P) of the tested lipase formulation with the bleach catalyst relative to the tested lipase formulation without the bleach catalyst:

$$ResP = P(\text{invention formulation with bleach catalyst}) / P(\text{invention formulation without bleach catalyst}).$$

ResPavg indicates the average relative performance compared to the conventional lipase formulation on each swatch type at all repetitions (3 repeated washes with 2 stains in each wash).

An improvement factor was taken as ResPavg for the invention formulation relative to the conventional formulation. A lipase formulation exhibits improved resistance towards the bleach catalyst if it has higher residual performance than the conventional lipase formulation.

Results

| | | Equest stains | | | | | | CFT |
|---|---|---|---|---|---|---|---|---|
| | | Hamburger grease | Lard | Margarine | Bacon grease | Butter | Avg Equest | stain CS67 |
| % ResPavg with 2.5 ppm Bleach catalyst | Invention formulation | 22 | 47 | 60 | 58 | 38 | 45 | 59 |
| | Conventional formulation | 0 | 25 | 20 | 8 | 26 | 16 | 37 |
| Improvement factor with 2.5 ppm Bleach catalyst | | NA | 1.9 | 2.9 | 7.0 | 1.4 | 3.3 | 1.6 |
| RPavg (%) | Lipex DR/ Lipex 100T | 117 | 95 | 120 | 68 | 80 | 96 | 106 |

The results for ResPavg for the conventional formulation are all 37% or less, indicating that the lipase is sensitive to the bleach catalyst.

The results for the improvement factor demonstrate that the lipase in the form of granules with a delayed-release coating is markedly less inhibited by the organic non-metal bleach catalyst than conventional granules. On average, the lipase with delayed-release coating was inhibited by 49-56% while the conventional granules were inhibited by 65-85%.

The results for RPavg demonstrate that the lipase performance of granules with delayed-release coating broadly matches that of conventional lipase granules although there is high variation in the performance values on the individual stains for both of the lipase samples.

Example 3: Release Profile

A lipase variant was granulated and coated as described in Example 1, and the release profile was determined according to Test Method 2 (Dissolution test), described above.

The time for release of 50% activity and 90% activity (T50 and T90) was found to be well above 400 seconds and well above 800 seconds, respectively.

For comparison, a conventional T-granulate of the same lipase variant coated with PEG (polyethylene glycol) and $CaCO_3$/kaolin was also tested. T50 and T90 of the conventional granulate were found to be 112 seconds and 242 seconds, respectively.

The invention claimed is:

1. A particulate composition comprising:
  a) particles comprising a source of organic peroxyacids, said particles having a time required to release 50% of the organic peroxyacids at 20° C. which is below 100 seconds, and
  b) particles comprising a bleach catalyst, and
  c) particles comprising
    i) a core comprising an enzyme which is a first-wash lipolytic enzyme, surrounded by
    ii) a delayed-release coating such that the particles have a time required to release 50% of the enzyme activity at 20° C. which is at least 100 seconds
  wherein the delayed-release coating comprises a substrate for the first-wash lipolytic enzyme selected from lipids, mono-, di- and triglycerides, palm oil, beeswax, jojoba oil, carnauba wax, polyesters, polyester block copolymers and polycaprolactone.

2. The particulate composition of claim 1 wherein the bleach catalyst is an organic bleach catalyst, a non-metal bleach catalyst or a catalytic metal complex.

3. The particulate composition of claim 1 wherein the enzyme is sensitive to the bleach catalyst.

4. The particulate composition of claim 1 wherein the enzyme activity is selected from the group consisting of a triacylglycerol lipase EC 3.1.1.3, cutinase EC 11.1.74, sterol esterase EC 3.1.1.13, and wax-ester hydrolase EC 3.1.1.50.

5. The particulate composition of claim 1 wherein the enzyme is a lipase having at least 90% identity with the wild-type lipase derived from *Thermomyces lanuginosus* strain DSM 4109.

6. The particulate composition of claim 1 wherein the enzyme comprises a lipase selected from variants of *Thermomyces lanuginosus* lipase variants having the mutations T231R and N233R.

7. The particulate composition of claim 1 wherein the enzyme comprises a cutinase, preferably selected from variants of *Pseudomonas mendocina* cutinase and *Humicola insolens* cutinase.

8. The particulate composition of claim 1, wherein the source of organic peroxyacids is a preformed peracid or a diacyl peroxide.

9. The particulate composition of claim 1, wherein the source of organic peroxyacids comprises a source of hydrogen peroxide and a bleach activator.

10. The particulate composition of claim 1 wherein the bleach catalyst is organic and is selected among iminium cations and polyions; iminium zwitterions; modified amines; modified amine oxides; N-sulphonyl imines; N-phosphonyl imines; N-acyl imines; thiadiazole dioxides; perfluoroimines; and cyclic sugar ketones.

11. The particulate composition of claim 1 wherein the bleach catalyst has a structure corresponding to the general formula below:

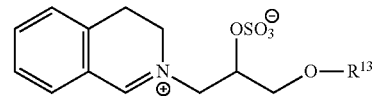

wherein $R^{13}$ is a branched alkyl group containing from three to 24 carbon atoms (including the branching carbon atoms) or a linear alkyl group containing from one to 24 carbon atoms.

12. The particulate composition of claim 1 wherein the delayed-release coating comprises a hydrophobic substance and a water-insoluble substance.

13. The particulate composition of claim 12 wherein the hydrophobic substance is a fat or wax.

14. The particulate composition of claim 12 wherein the water-insoluble substance is titanium dioxide, calcium carbonate or kaolin.

15. The particulate composition of claim 1 wherein the delayed-release coating comprises a substrate for the enzyme.

16. The particulate composition of claim 1 wherein the enzyme-containing particles (c) further comprise an additional top coating selected from the group consisting of polyethylene glycol, polyvinyl alcohol and hydroxypropyl methyl cellulose.

17. The particulate composition of claim 1 wherein the enzyme-containing particles (c) have a time for 50% release of enzyme in detergent solution at 20° C. of at least 300 seconds.

18. The particulate composition of claim 1 wherein the enzyme-containing particles (c) have a time required for release of 50% of the enzyme activity which is at least 1.5 times longer than the time required for similar enzyme granules without the coating.

19. The particulate composition of claim 1 wherein the enzyme-containing particles (c) have a time required for release of 90% of the enzyme activity which is at least 1.5 times longer than the time required for similar enzyme granules without the coating.

* * * * *